United States Patent
Yoshimura et al.

(10) Patent No.: US 7,339,062 B2
(45) Date of Patent: Mar. 4, 2008

(54) METHOD FOR PRODUCING A 3,5-DIHYDROXY-6-HEPTENOATE

(75) Inventors: Yuji Yoshimura, Yamaguchi (JP); Masami Yasukawa, Chiba (JP); Syuji Morikiyo, Yamaguchi (JP); Hiroo Matsumoto, Chiba (JP); Yasutaka Takada, Chiba (JP); Michiaki Adachi, Chiba (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 10/528,179

(22) PCT Filed: Sep. 11, 2003

(86) PCT No.: PCT/JP03/11643

§ 371 (c)(1),
(2), (4) Date: Mar. 17, 2005

(87) PCT Pub. No.: WO2004/026838

PCT Pub. Date: Apr. 1, 2004

(65) Prior Publication Data

US 2006/0167260 A1    Jul. 27, 2006

(30) Foreign Application Priority Data

Sep. 20, 2002  (JP) ............................. 2002-275015

(51) Int. Cl.
*C07D 215/04*  (2006.01)
*C07D 215/12*  (2006.01)

(52) U.S. Cl. .................. 546/173; 546/153; 546/174

(58) Field of Classification Search ................ 546/173, 546/174, 152
See application file for complete search history.

(56) References Cited

U.S. PATENT DOCUMENTS

| | | | |
|---|---|---|---|
| 5,939,552 A * | 8/1999 | Ikeda et al. ................. | 546/152 |
| 6,835,838 B2 * | 12/2004 | Chen et al. ................. | 546/173 |
| 6,946,557 B2 * | 9/2005 | Onishi et al. ............... | 546/173 |

FOREIGN PATENT DOCUMENTS

EP    0 520 406    12/1992

EP    0 747 341    12/1996

OTHER PUBLICATIONS

Nagamatsu, J of Chromatography A, vol. 832, pp. 55-65, 1999.*
Gebauer, CA 129:197349, abstract only of J of Chrm Sci, vol. 36(8), pp. 383-387, 1998.*
Davey, CA 117:229369, abstract only of Analy Biochem, vol. 206(2), pp. 323-327, 1992.*
Iwuagwu, CA 105:179553, abstract only of Nigerial J of PHarm Sci, 2(1), pp. 83-90, 1986.*
Peng, CA 99:110835, abstract only of J of Liq Chrom vol. 6(8), pp. 1499-1511, 1983.*
Wang, CA 97:203288, abstract only of Yaoxue Xuebao, vol. 17(8), pp. 603-608, 1982.*
Hara, CA 93:185599, abstract only of HRC7CC J of High Res Chrom, vol. 3(4), pp. 193-194, 1980.*
Thiem, CA 89:175853, abstract only of J of Chrom, vol. 155(1), pp. 107-118, 1978.*

\* cited by examiner

*Primary Examiner*—D. Margaret Seaman
(74) *Attorney, Agent, or Firm*—Oblon, Spivak, McClelland, Maier & Neustadt, P.C.

(57) ABSTRACT

A method for producing an alkyl (3R,5S)-7-[2-cyclopropyl-4-(4-fluorophenyl)quinolin-3-yl]-3,5-dihydroxy-6-heptenoate of the formula (1) (wherein R is a $C_{1-4}$ alkyl group), which is an intermediate for a cholesterol-reducing agent (a HMG-CoA reductase inhibitor), etc. A solution containing a compound of the formula (1) is subjected to liquid chromatography treatment using silica gel as the packing material, to separate its epimers contained therein.

(1)

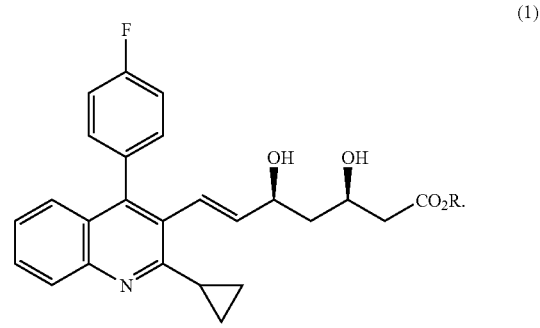

7 Claims, 3 Drawing Sheets

True Moving Bed (TMB)

Concept of Simulated Moving Bed (SMB)

METHOD FOR PRODUCING A 3,5-DIHYDROXY-6-HEPTENOATE

TECHNICAL FIELD

The present invention relates to a method for producing an alkyl (3R,5S)-7-[2-cyclopropyl-4-(4-fluorophenyl)quinolin-3-yl]-3,5-dihydroxy-6-heptenoate of the formula (1) (wherein R is a $C_{1-4}$ alkyl group), which is a compound useful as an intermediate for pharmaceuticals and which can be used for the production of a cholesterol-reducing agent (a HMG-CoA reductase inhibitor), etc. (JP-A-1-279866, EP304063A or U.S. Pat. No. 5,011,930).

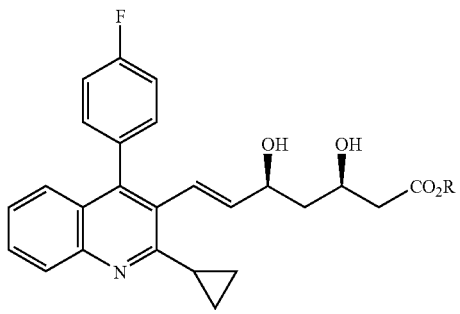

(1)

BACKGROUND ART

As methods for producing an alkyl (3R,5S)-7-[2-cyclopropyl-4-(4-fluorophenyl)quinolin-3-yl]-3,5-dihydroxy-6-heptenoate of the formula (1) (wherein R is a $C_{1-4}$ alkyl group), the following methods (a) to (c) by optical resolution of its racemic modification and the following methods (d) to (f) by an asymmetric synthesis, are known.

(a) A method for producing it by an optical resolution of its racemic modification by means of a high performance liquid chromatography (HPLC) column (such as CHIRAL-CEL OF, manufactured by Daicel Chemical Industries, Ltd.) for separation of optical isomers (e.g. International Patent Publication No. 95/23125, U.S. Pat. No. 5,939,552).

(b) A method for optical resolution of a racemic modification by means of an enzyme (e.g. JP-A-2001-352996).

(c) A method wherein the racemic modification is hydrolyzed, and the obtained carboxylic acid are subjected to optical resolution by means of a resolving agent such as an optically active α-methylbenzylamine, followed by esterification (e.g. JP-A-5-148237, U.S. Pat. No. 5,284,953).

(d) A method for producing it by means of a chiral synthon of the formula (4) (e.g. JP-A-8-127585).

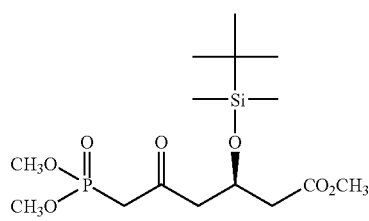

(4)

(e) A method of chemically selectively reducing an alkyl 7-[2-cyclopropyl-4-(4-fluorophenyl)quinolin-3-yl]-5-hydroxy-3-oxo-6-heptenoate of the formula (5) (wherein R is as defined above) obtainable by e.g. an asymmetric aldol reaction (e.g. JP-A-8-92217). The compound of the formula (5) can be obtained by an asymmetric synthesis (e.g. International Patent Publication No. 03/042180).

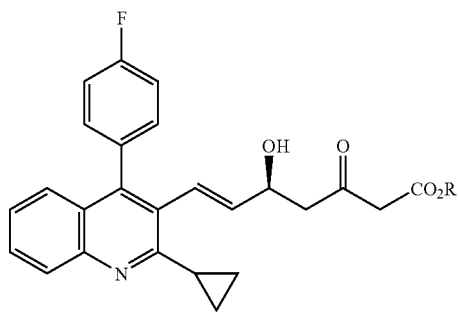

(5)

(f) A method of selectively reducing an optically active compound of the formula (5) or an alkyl 7-[2-cyclopropyl-4-(4-fluorophenyl)quinoline-3,5-dioxo-6-heptenoate of the formula (6) (wherein R is as defined above) by a biochemical technique (e.g. International Patent Publication No. 02/063028).

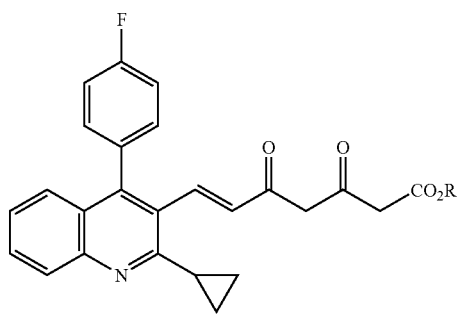

(6)

By the above-mentioned method (a) or (b), by recrystallizing the racemic modification corresponding to the compound of the formula (1), its epimers (a 1:1 mixture of compounds of the formulae (2) and (3)) can easily be removed, whereby the compound of the formula (1) of high purity can be obtained without separating the epimers after the optical resolution. However, such a technique by optical resolution of the racemic modification has an essential problem that its antipode (an alkyl (3S,5R)-7-[2-cyclopropyl-4-(4-fluorophenyl)quinolin-3-yl]-3,5-dihydroxy-6-heptenoate) will be wasted. By the method (c), the two types of epimers can be removed together with the antipode in the step for the resolution of diastereomers, whereby no purification of the racemic modification is required. However, this method is also essentially a resolution method of the racemic modification and thus has the same essential drawback as the methods (a) and (b).

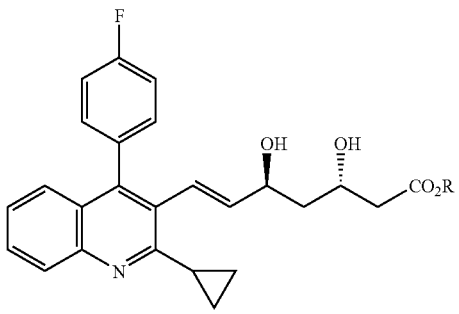

(2)

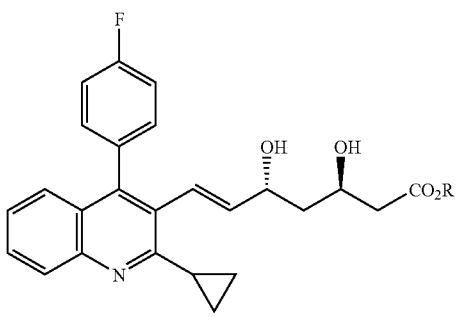

(3)

The above methods (c) to (f) are production methods via an optically active compound of the formula (5) or (7), but neither the chemical reaction method nor the biochemical reduction method is a completely selective reaction, whereby inclusion of a small amount of epimers is unavoidable. To secure the quality useful as an intermediate for pharmaceuticals, it is necessary to remove such epimers, but, as is different from the racemic modification, the optically active substance of the formula (1) is a compound which is extremely difficult to purify by recrystallization. A purification method by leading it to a p-toluene sulfonate or the like, has also been tried, but the purpose has not been accomplished in any case for such a reason that lactone-modification tends to proceed during the purification operation.

However, by each of the asymmetric synthesis and the chiral synthon method, the optically active compound of the formula (5) or (7) can be produced with a high optical purity, whereby the antipode will not be wasted. Accordingly, if it can be established as an industrial production method, the economical effects will be substantial. Therefore, it has been desired to establish an efficient purification method for the compound of the formula (1).

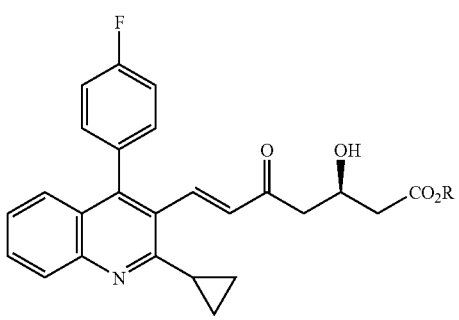

(7)

DISCLOSURE OF THE INVENTION

The present inventors have studied separation of the optically active substance of the formula (1) and its epimers and as a result, have found it possible to separate them by employing a chromatography treatment and using, as its packing material, silica gel which preferably has certain specific physical properties, and preferably by using a mixture of hexane/isopropyl alcohol as the eluent.

Further, the present inventors have found that by the method of employing a simulated moving bed system for the chromatography treatment in such a case, it is possible to substantially reduce the amount of the solvent to be used, which used to be a problem in the conventional chromatography treatment, and it is possible to reuse the eluent recovered in the chromatography treatment, whereby the method can be carried out industrially advantageously.

The present invention is based on such discoveries and provides the following:

1. A method for producing a compound of the formula (1):

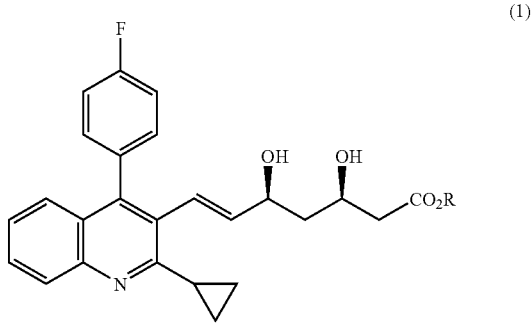

(1)

which comprises subjecting a solution containing an alkyl (3R,5S)-7-[2-cyclopropyl-4-(4-fluorophenyl)quinolin-3-yl]-3,5-dihydroxy-6-heptenoate of the formula (1) (wherein R is a $C_{1-4}$ alkyl group) to liquid chromatography treatment using silica gel as the packing material, to separate its epimers contained therein.

2. The method according to Item 1, wherein in the chromatography treatment, a mixed solvent comprising hexane/isopropyl alcohol is used as an eluent.

3. The method according to Item 2, wherein the ratio of hexane/isopropyl alcohol in the mixed solvent is from 99/1 to 50/50 in a volume ratio.

4. The method according to any one of Items 1 to 3, wherein the silica gel as the packing material has an average particle diameter of from 0.1 μm to 10 mm and an average pore diameter of from 1 nm to 100 μm.

5. The method according to any one of Items 1 to 4, wherein the chromatography treatment is a treatment employing a simulated moving bed apparatus.

6. The method according to Item 5, wherein either component of the eluent is added to a distillate of the extract and raffinate recovered in the chromatography treatment, to adjust the compositional ratio of the distillate to the compositional ratio of the eluent before use, and the distillate so adjusted, is reused.

7. The method according to any one of Items 1 to 6, wherein R in the compound of the formula (1) is an ethyl group.

Zone I: between the eluent flow path and the extract flow path

Zone II: between the extract flow path and the feed flow path

Zone III: between the feed flow path and the raffinate flow path

Zone IV: between the raffinate flow path and the eluent flow path

Figure 2:
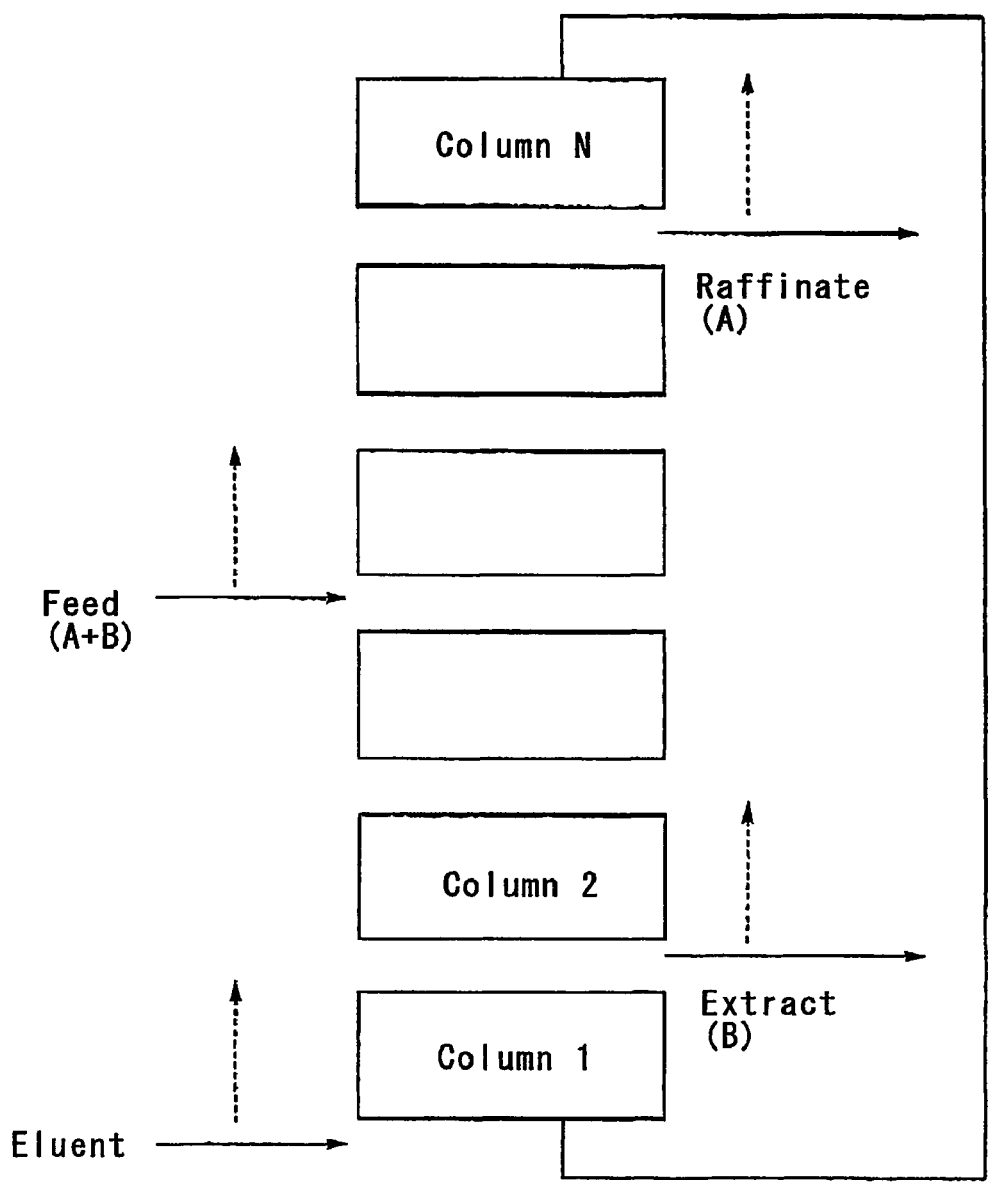

FIG. 2 is a view showing the concept of a simulated moving bed (SMB).

Figure 3:
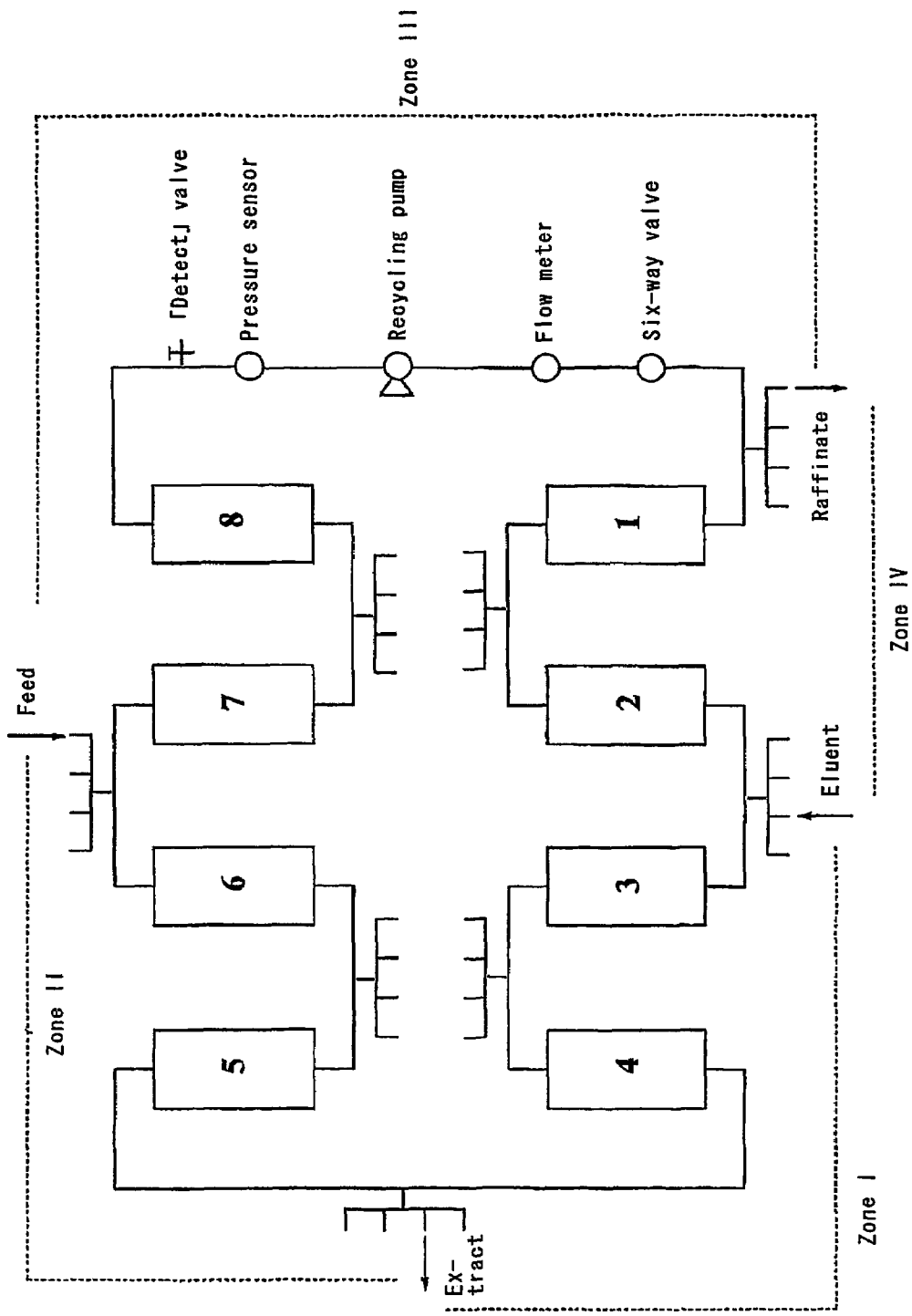

FIG. 3 is a view illustrating a 4-zone simulated moving bed (SMB) of one embodiment of the apparatus to carry out the method of the present invention.

BEST MODE FOR CARRYING OUT THE INVENTION

In the present invention, the object to be separated and purified is an alkyl (3R,5S)-7-[2-cyclopropyl-4-(4-fluorophenyl)quinolin-3-yl]-3,5-dihydroxy-6-heptenoate of the formula (1) (wherein R is a $C_{1-4}$ alkyl group) containing one or both of an alkyl (3S,5S)-7-[2-cyclopropyl-4-(4-fluorphenyl)quinolin-3-yl]-3,5-dihydroxy-6-heptenoate of the formula (2) (wherein R is as defined above) and an alkyl (3R,5R)-7-[2-cyclopropyl-4-(4-fluorophenyl)quinolin-3-yl]-3,5-dihydroxy-6-heptenoate of the formula (3) (wherein R is as defined above).

The alkyl group R may, for example, be a methyl group, an ethyl group, a propyl group, an isopropyl group, a butyl group, a sec-butyl group, an isobutyl group or a tert-butyl group. Among them, the alkyl group is preferably one having 1 or 2 carbon atoms, particularly preferably an ethyl group.

The proportions of the compounds of the formulae (1), (2) and (3) to be contained, are not particularly limited. However, the higher the proportion of the compound of the formula (1), the higher the separation efficiency, whereby one having a high purity can be obtained.

The compounds of the formulae (2) and (3) are in the relation of enantiomers to each other, and their chromatographic behaviors are the same, and the ratio of the two compounds may be 1:1 or different.

Further, there is no particular limitation to the optical purity of the compound of the formula (1), but from the viewpoint of the production of an intermediate for pharmaceuticals as the object of the present invention, an optical purity of at least 95% e.e. is preferred.

In the chromatography treatment of the present invention, the object can be accomplished by using either one of a common batch system using a single column (see Example 2) and a simulated moving bed method wherein continuous separation is possible (see Examples 3 to 6). However, as the process for carrying out the method of the present invention, it is more preferred to employ a simulated moving bed method. The simulated moving bed method is industrially used, for example, in the separation of pure p-xylene from a mixture of xylenes (JP-B-42-15681, etc.), and its concept will be briefly explained.

Figure 1:
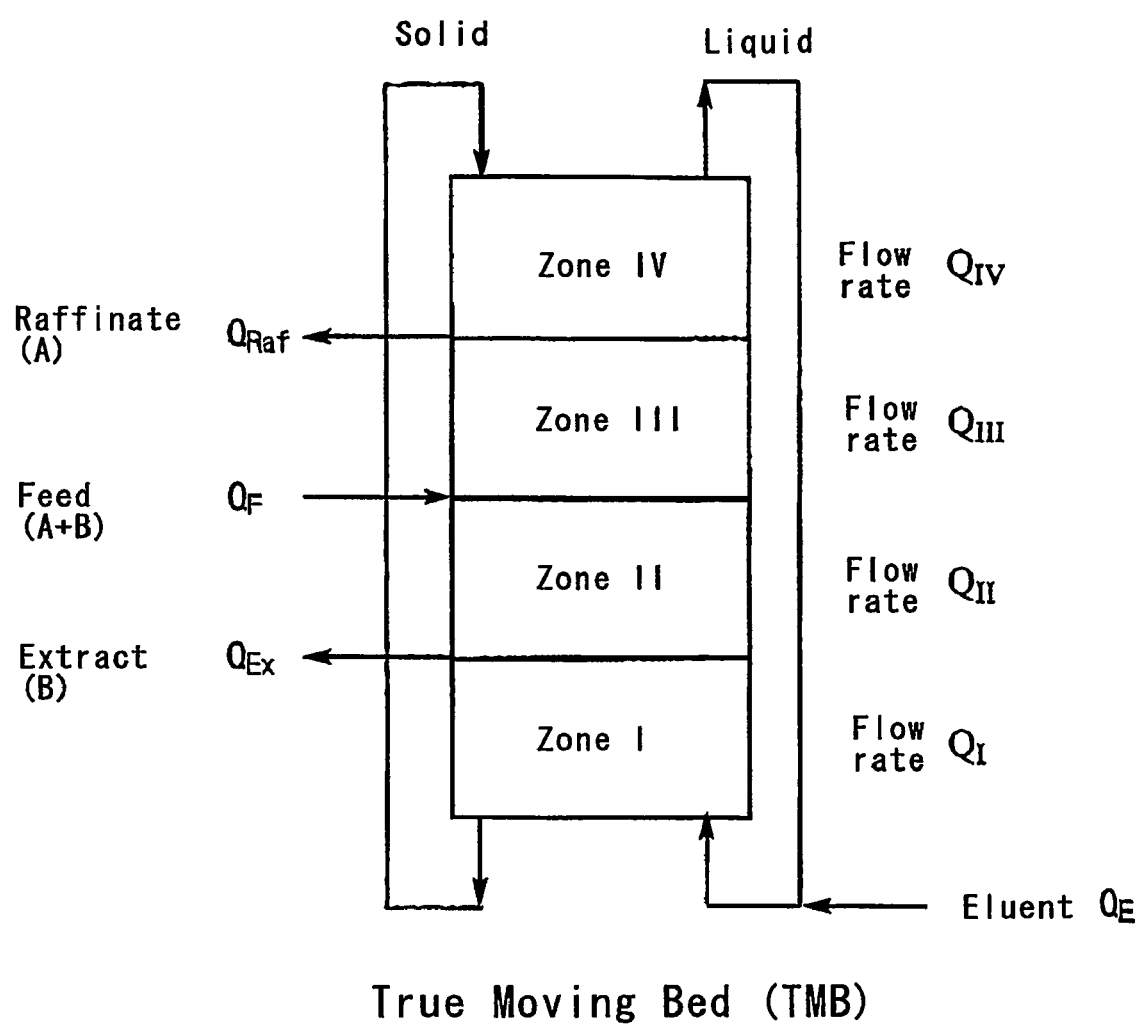
FIG. 1 is a view illustrating a true moving bed (TMB). The definitions of zones I to IV are as follows.

The concept of the simulated moving bed (SMB) may readily be understood by examining a true moving bed method (TMB) as shown in FIG. 1. The true moving bed method (TMB) is designed for counter-current adsorption separation treatment and is constituted by 4-zones, wherein the solid and the liquid flow in inverse directions. There are two inlet paths, whereby the solution (the feed) to be separated and the eluent are continuously introduced. From two outlet flow paths (for the extract and the raffinate), pure products are continuously recovered. The liquid coming out from zone IV is returned (recycled) to zone I, and the solid coming out from zone I is returned (recycled) to zone IV. For example, in the case of a two component mixture (A+B) wherein component A has a shorter retention time, the operation conditions (the flow rates in the respective zones) are set so that component A moves upward, and component B moves downward. Component A and component B can be recovered as pure products, respectively, from the raffinate outlet and the extract outlet. However, in such a true moving bed method (TMB), the operation is practically very difficult, since it is necessary to circulate the solid adsorbent.

Now, on the basis of the true moving bed (TMB), the simulated moving bed (SMB) is considered. In the simulated moving bed (SMB), several fixed columns are connected in series, and introducing points and recovering points are properly moved (FIG. 2) to let counter-current actually take place. Accordingly, each flow path for the feed, the eluent, the extract or the raffinate, is moved for every column (or every few columns) at constant time intervals in the flow direction of the solution. A specific method will be described in Examples given hereinafter.

In the chromatography treatment of the present invention, as the packing material, silica gel may be advantageously used by virtue of its separation characteristics. Silica gel is inexpensive, and one having a constant quality can readily be available, such being particularly advantageous. In the present invention, if a packing material other than silica gel, such as alumina, is used, the compound of the formula (1) is likely to undergo lactonization, such being undesirable. Further, if a silicate, diatomaceous earth or the like is used, inclusion of impurities such as metals or organic substances, is likely, such being undesirable, particularly when the compound of the present invention will be used as a material for pharmaceuticals. As silica gel, pulverized one may be used, but spherical one is preferred. The silica gel preferably has an average particle size of from 0.1 μm to 10 mm, particularly preferably from 1 μm to 300 μm, more preferably from 5 μm to 100 μm The average pore diameter of the silica gel is preferably from 1 nm to 100 μm, particularly preferably from 5 nm to 5 μm. Here, the average particle diameter, median diameter or mode diameter, is obtained by a light scattering/laser diffraction method, and the average micropore diameter is obtained by a gas adsorption method or mercury porosimeter.

As the eluent for chromatography, a mixed solvent of hydrocarbon/alcohol may, for example, be used. Particularly preferred is a mixture of hexane/isopropyl alcohol. However, the eluent is not particularly limited so long as it presents no adverse effect to the stability of the packing material. In a case where a mixed solvent of hexane/isopropyl alcohol is to be employed, the ratio of hexane/isopropyl alcohol is usually within a range of from 99/1 to 50/50, preferably from 98/2 to 70/30, more preferably from 96/4 to 85/15, in a volume ratio. A third solvent may be incorporated, but in the case of chromatography treatment, particularly in the case of the simulated moving bed method, the composition is preferably as simple as possible for the recovery and reuse of the solvents.

From the recovered eluent (the raffinate and the extract in the simulated moving bed method), the solvents can be distilled and reused. The composition of the solvents may be analyzed, for example, by gas chromatography, and either component of the eluent is added thereto to adjust the composition to the predetermined composition of the eluent, whereupon the adjusted mixed solvent can readily be reused for column separation (see Example 6). For the above distillation of the solvents, an evaporator or condenser may be employed. Usually, a thin membrane type condenser can suitably be used.

In the chromatography treatment of the present invention, the column temperature is preferably set to be a constant temperature (for example, at 40° C. as in Example 1) within a range of from 10 to 50° C., preferably within a range of from 20 to 45° C. Other conditions for carrying out the chromatography treatment such as the supply rates of the eluent and the solution containing a mixture of isomers, the flow rates at the discharge outlets of the raffinate and the extract, the time for switching the column, the column pressure, etc., are properly set in accordance with the chromatography techniques known to those skilled in the art, so that they are suitable for the conditions for e.g. the packing material, the eluent, the production quantity, etc.

EXAMPLES

Now, the present invention will be described in detail with reference to Examples, but it should be understood that the present invention is by no means restricted to such specific Examples.

In the following Examples, a compound of the formula (1), wherein R is an ethyl group is used, and this compound will be referred to as (3R,5S)DOLE(1); the compound of the formula (2) will be referred to as (3S,5S)DOLE(2); and the compound of the formula (3) will be referred to as (3R,5R)DOLE(3).

Example 1

Using a commercially available silica gel column for high performance liquid chromatography (HPLC) analysis, a 1:1 mixture of (3S,5S)DOLE(2) and (3R,5S)DOLE(1) was separated. The conditions are shown below.
Column: YMC Pack Sil S-5 (manufactured by YMC Company, diameter: 4.6 mm, length: 250 mm, packing material: silica gel having an average particle diameter of 5 μm and an average pore diameter of 12 nm)
Eluent: hexane/isopropyl alcohol=20/1
Temperature: 40° C.
Flow rate: 1.0 mL/min
Detection: UV (254 nm)
Retention time: (3S,5S)DOLE(2) 11.4 min
(3R,5S)DOLE(1) 13.7 min Example 2

Using YMC-Pack SIL as a commercially available silica gel column, batch system separation by HPLC was carried out. The conditions were as follows:
Column: YMC Pack Sil (manufactured by YMC Company, diameter: 2 cm, length: 25 cm, packing material: silica gel having an average particle diameter of 10 μm and an average pore diameter of 12 nm)
Eluent: hexane/isopropyl alcohol=95/5
Temperature: 40° C.
Flow rate: 8.0 mL/min
The sample used for separation was 1.01 g of (3R,5S)DOLE(1) containing 3% by mass of (3S,5S)DOLE(2). This sample was dissolved in a solvent having the same composition as the eluent, and the concentration was adjusted to 3% w/v, and 2 mL of the adjusted sample was injected, whereupon a fraction (containing (3S,5S)DOLE(2)) corresponding to the retention time of from 9.42 min to 10.54 min and a fraction (containing (3R,5S)DOLE(1)) corresponding to a retention time of from 11.03 min to 13.03 min, were collected. This operation was repeated 17 times, whereupon the respective solvents were distilled off, whereby 892 mg (yield: 89%) of (3R,5S)DOLE(1) having no epimers detected by the HPLC analysis and 29.0 mg (yield: 2.8%) of (3S,5S)DOLE(2) having a HPLC relative area percentage of 96.5%, were obtained. The conditions for the HPLC analysis were the same as in Example 1.

(3R,5S)DOLE (1)
$^1$H-NMR (CDCl$_3$, TMS) δ (ppm): 1.01-1.05 (2H, m, C9+C10), 1.27-1.35 (3H, m, C9+C10+C4), 1.29 (3H, t, J=7.2 Hz, Et), 1.43-1.55 (1H, m, C4), 2.36-2.45 (3H, m, C8+C2), 3.17 (1H, d, J=1.7 Hz, OH), 3.64 (1H, d, J=2.7 Hz, OH), 4.08-4.23 (1H, m, C3), 4.19 (2H, q, J=7.2 Hz, Et), 4.38-4.43 (1H, m, C5), 5.58 (1H, dd, J=6.2, 16.1 Hz, C6), 6.64 (1H, dd, J=1.3, 16.1 Hz, C7), 7.12-7.23 (4H, m, Ar), 7.29-7.36 (2H, m, Ar), 7.58 (1H, ddd, J=2.1, 6.3, 8.5 Hz, C17), 7.95 (1H, d, J=8.3 Hz, C18).

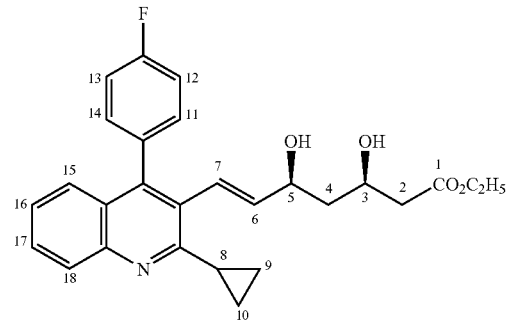

(3S,5S)DOLE (2)
$^1$H-NMR (CDCl$_3$, TMS) δ (ppm): 1.03 (2H, dd, J=2.8, 8.0 Hz, C9+C10), 1.29 (3H, t, J=7.2 Hz, Et), 1.27-1.36 (2H, m, C9+C10), 1.37-1.44 (1H, m, C4), 1.62-1.71 (1H, m, C4), 2.33-2.49 (3H, m, C2+C8), 2.95 (1H, d, J=5.5 Hz, 3-OH), 3.47 (1H, brs, 5-OH), 3.97-4.08 (1H, m, C3), 4.20 (2H, q, J=7.2 Hz, Et), 4.39-4.49 (1H, m, C5), 5.66 (1H, dd, J=5.5, 16.2 Hz, C6), 6.70 (1H, dd, J=1.4, 16.0 Hz, C7), 7.13-7.33 (6H, m, Ar), 7.58 (1H, ddd, J=3.0, 5.2, 8.3 Hz, C17), 7.95 (1H, d, J=8.5 Hz, C18).

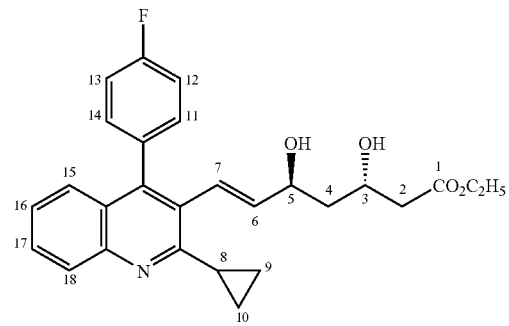

Example 3

(3R,5S)DOLE(1) containing 3% by mass of (3S,5S)DOLE(2) was dissolved in a mixed liquid of hexane/isopropyl alcohol (in a volume ratio of 20/1), and a starting material liquid (feed) having a concentration of 30 g/L was prepared.

Eight columns having an inner diameter of 3 cm and a length of 10 cm and having a commercially available silica gel (YMC-SIL-120-S15/30 (average particle diameter:

15/30 μm, average pore diameter: 12 nm)) packed to the simulated moving bed type fractionation apparatus LICOSEP-LAB (manufactured by Novasep Company) as shown in FIG. 3, were connected in series, and fractionation was initiated by such an apparatus construction that the feed was introduced at position 7, the eluent was introduced at position 3, the extract was recovered at position 5 and the raffinate is recovered at position 1. Using a mixed liquid of hexane/isopropyl alcohol (in a volume ratio of 20/1) as the eluent, the operation temperature was set to be 35° C., and the feed was set to be 30 g/L. The operation was carried out at a recycling flow rate of 98.6 mL/min, at a feed flow rate of 4.14 mL/min, at a raffinate flow rate of 13.56 mL/min, at an extract flow rate of 12.84 mL/min, at an eluent flow rate of 22.26 mL/min and for a switching time of 2.68 min, whereby from the extract, (3R,5S)DOLE(1) having a HPLC purity of 99.98% (refer to Example 1 for the analytical conditions) was obtained. On the other hand, from the raffinate, a mixture of (3S,5S)DOLE(2) (HPLC purity of 96.83%) and (3R,5S)DOLE(1) (HPLC purity of 3.17%) was obtained. Thus, (3R,5S)DOLE(1) was separated substantially quantitatively.

Example 4

In Example 3, the operation was carried out by changing the recycling flow rate to 132.12 mL/min, the feed flow rate to 5.55 mL/min, the raffinate flow rate to 18.17 mL/min, the extract flow rate to 17.21 mL/min, the eluent flow rate to 29.83 mL/min and the switching time to 2.00 min, whereby from the extract, (3R,5S)DOLE(1) having a purity of 99.96% was obtained. On the other hand, from the raffinate, a mixture of (3S,5S)DOLE(2) (HPLC purity of 88.14%) and (3R,5S)DOLE(1) (HPLC purity of 11.86%) was obtained.

Example 5

The same simulated moving bed apparatus as in Example 3, was used. The ratio of the mixed liquid of hexane/isopropyl alcohol was changed to 20/3 in a volume ratio, and the concentration of the starting material liquid (feed) was also changed to 45 g/L.

The operation was carried out at a recycling flow rate of 132.00 mL/min, at a feed flow rate of 5.66 mL/min, at a raffinate flow rate of 21.79 mL/min, at an extract flow rate of 18.58 mL/min, at an eluent flow rate of 34.71 mL/min for a switching time of 0.83 min, whereby from the extract, (3R,5S)DOLE(1) having a HPLC purity of 99.66% was obtained ((3S,5S)DOLE(2): 0.26%). On the other hand, from the raffinate, a mixture of (3S,5S)DOLE(2) (HPLC purity of 38.36%) and (3R,5S)DOLE(1) (HPLC purity of 60.38%) was obtained.

Example 6

The same simulated moving bed apparatus as in Example 3 was used, the ratio of the mixed liquid of hexane/isopropyl alcohol was adjusted to be 20/3 in a volume ratio, and the concentration of the starting material liquid (feed) was adjusted to be 45 g/L.

The operation was carried out at a recycling flow rate of 132.00 mL/min, at a feed flow rate of 5.66 mL/min, at a raffinate flow rate of 20.79 mL/min, at an extract flow rate of 19.58 mL/min, at an eluent flow rate of 34.71 mL/min for a switching time of 0.83 min, whereby from the extract, (3R,5S)DOLE(1) having a HPLC purity of 99.31%, was obtained ((3S,5S)DOLE(2): 0.35%). On the other hand, from the raffinate, a mixture of (3S,5S)DOLE(2) (HPLC purity of 68.99%) and (3R,5S)DOLE(1) (HPLC purity of 30.79%) was obtained.

Then, the extract and the raffinate obtained by the above operation corresponding to about 40 cycles were, respectively, concentrated by thin film condensers, and the respective concentrates were put together to recover about 9.87 L. The compositional ratio of the distillate was analyzed by gas chromatography, and 2154 mL of hexane was added so that the compositional ratio of hexane/isopropyl alcohol would be 20/3. Further, 5 L of a mixed liquid of hexane/isopropyl alcohol (20/3) freshly prepared, was added, to obtain a total of about 17 L of an eluent.

Using this liquid, a starting material liquid of 45 g/L was prepared, and separation was again carried out by the same simulated moving bed apparatus as in Example 3.

The operation was carried out at a recycling flow rate of 132.00 mL/min, at a feed flow rate of 5.66 mL/min, at a raffinate flow rate of 20.79 mL/min, at an extract flow rate of 19.58 mL/min, at an eluent flow rate of 34.71 mL/min for a switching time of 0.83 min, whereby from the extract, (3R,5S)DOLE(1) having a HPLC purity of 99.22% was obtained ((3S,5S)DOLE(2): 0.21%). On the other hand, from the raffinate, a mixture of (3S,5S)DOLE(2) (HPLC purity of 30.51%) and (3R,5S)DOLE(1) (HPLC purity of 68.50%) was obtained.

A similar operation was further repeated twice.

In the second time, from the extract, (3R,5S)DOLE(1) having a HPLC purity of 99.12% was obtained ((3S, 5S9DOLE(2): 0.41%). On the other hand, from the raffinate, a mixture of (3S,5S)DOLE(2) (HPLC purity of 34.07%) and (3R,5S)DOLE(1) (HPLC purity of 65.83%) was obtained.

In the third time, from the extract, (3R,5S)DOLE(1) having a HPLC purity of 99.33% was obtained ((3S,5S) DOLE(2): 0.45%). On the other hand, from the raffinate, a mixture of (3S,5S)DOLE(2) (HPLC purity of 28.12% and (3R,5S)DOLE(1) (HPLC purity of 71.78%) was obtained.

From the foregoing Examples, it was confirmed that the desired products can be separated even by the recovered solvents, and it is evident that the chromatography method is an industrially superior method.

INDUSTRIAL APPLICABILITY

According to the present invention, it is possible to provide a novel method for efficiently separating an alkyl (3R,5S)-7-[2-cyclopropyl-4-(4-fluorphenyl)quinolin-3-yl]-3,5-dihydroxy-6-heptenoate epimer useful as an intermediate for pharmaceuticals and its epimer by specific chromatography treatment. According to the method of the present invention, the desired product can be obtained in good yield without wasting the antipode by conventional optical resolution, whereby an economical effect is substantial, and further, the eluent used for the chromatography treatment, can be recovered and reused, whereby an excellent industrial production method will be provided.

What is claimed is:

1. A method for producing a compound of the formula (1) by separating its epimers contained therein:

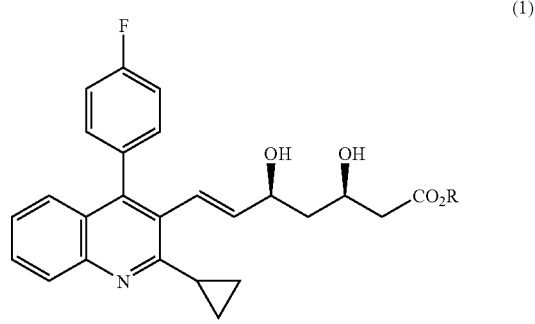

which comprises subjecting a solution containing an alkyl (3R,5S)-7-[2-cyclopropyl-4-(4-fluorophenyl)quinolin-3-yl]-3,5-dihydroxy-6-heptenoate of the formula (1) (wherein R is a $C_{1-4}$ alkyl group) to liquid chromatography treatment using uncoated silica gel as the packing material.

2. The method according to claim 1, wherein in the chromatography treatment, a mixed solvent comprising hexane/isopropyl alcohol is used as an eluent.

3. The method according to claim 2, wherein the ratio of hexane/isopropyl alcohol in the mixed solvent is from 99/1 to 50/50 in a volume ratio.

4. The method according to any one of claims 1 to 3, wherein the uncoated silica gel as the packing material has an average particle diameter of from 0.1 μm to 10 mm and an average pore diameter of from 1 nm to 100 μm.

5. The method according to any one of claims 1 to 3, wherein the chromatography treatment is a treatment employing a simulated moving bed apparatus.

6. The method according to claim 5, wherein either component of the eluent is added to a distillate of the extract and raffinate recovered in the chromatography treatment, to adjust the compositional ratio of the distillate to the compositional ratio of the eluent before use, and the distillate so adjusted, is reused.

7. The method according to any one of claims 1 to 3, wherein R in the compound of the formula (1) is an ethyl group.

* * * * *